United States Patent [19]

Burkhardt et al.

[11] Patent Number: 4,810,470

[45] Date of Patent: Mar. 7, 1989

[54] VOLUME INDEPENDENT DIAGNOSTIC DEVICE

[75] Inventors: Alan E. Burkhardt; Marvin A. Genshaw; Lon R. Stover, all of Elkhart, Ind.

[73] Assignee: Miles Inc., Elkhart, Ind.

[21] Appl. No.: 63,925

[22] Filed: Jun. 19, 1987

[51] Int. Cl.4 .................... G01N 31/22; G01N 33/52; G01N 33/53

[52] U.S. Cl. ........................................ 422/56; 422/58; 422/57; 436/165

[58] Field of Search ............................ 422/56, 57, 58; 436/165, 169

[56] References Cited

U.S. PATENT DOCUMENTS 3,917,453 11/1975 Milligan et al. ...................... 422/56
4,647,430 3/1987 Zweig ..................................... 42/58

*Primary Examiner*—Barry S. Richman
*Assistant Examiner*—Lyle Alfandary-Alexander
*Attorney, Agent, or Firm*—Roger N. Coe

[57] ABSTRACT

A process and device for quantitative determination of analyte concentrations in liquid samples. The device includes one or more bibulous matrices constructed and arranged to essentially eliminate sample volume sensitivity from analyte determinations. In accordance with the present invention, the device includes one or more test reagent-treated bibulous matrices covered at least partially by an impermeable coating or film. A liquid sample is applied to the uncovered portion of the bibulous matrix such that the liquid sample is metered into the bibulous matrix by the impermeable coating or film. The sample chromatographs through the bibulous matrix until the matrix is saturated with liquid. The process is essentially sample volume independent, providing more uniform and accurate quantitative analyte determinations.

11 Claims, 11 Drawing Sheets

VOLUME INDEPENDENT DIAGNOSTIC DEVICE

FIELD OF THE INVENTION

The present invention relates to a process and device for quantitatively determining analyte concentrations in liquids. More particularly, the present invention relates to an improved method of quantitatively determining the concentration of specific analytes in liquids, whereby assay sensitivity to the amount of test sample applied to the device is essentially eliminated. Overall, more accurate and more reproducible analyte determinations result.

BACKGROUND OF THE INVENTION

Presently, there are numerous test devices available to simply and rapidly test liquids for the presence or absence of a particular analyte. For example, in regards to body fluids, tests are available to detect glucose, uric acid or protein in urine and to detect glucose, potassium ion or cholesterol in blood. Historically, most of the available diagnostic test devices have been sensitive to the volume of the test sample, as well as to the concentration of the particular analyte of interest.

The medical profession has provided an impetus to growth in this field by requiring analyte determinations that yield accurate and reproducible results and that can be performed quickly and cheaply. Such test methods are especially desirable in small or private medical offices, where fast and accurate results are required, but the volume of assay samples is low enough to preclude the investment in expensive diagnostic devices. In addition, the medical profession requires simple and essentially foolproof diagnostic tests, that are performable by relatively untrained personnel, due to the expense of having highly qualified personnel perform these routine assays.

As a result, several test methods have been developed that are inexpensive, fast, and easy to perform. Among the most widely used diagnostic devices are the "dip-and-read" type devices. These devices are widely used in the chemical analysis of biological fluids. For example, numerous physiological functions can be monitored merely by dipping a reagent strip device into a sample of body fluid, such as urine, and observing a detectable response, such as a change in color or a change in the amount of light reflected from or absorbed by the test device.

Many of the "dip-and-read" test devices for detecting body fluid components are capable of making quantitative or at least semiquantitative measurements. Thus, by measuring the response after a predetermined time, an analyst can obtain not only a positive indication of the presence of a particular analyte in a test sample, but also an estimate of how much of the analyte is present. Such test devices provide the physician with a facile diagnostic tool as well as the ability to gauge the extent of disease or of bodily malfunction.

Test devices such as these usually comprise one or more bibulous matrices, such as absorbent paper, having incorporated therein a particular test reagent that produces a detectable response, e.g., a color change, in the presence of a specific test sample analyte. Depending on the test reagent system incorporated into a particular bibulous matrix, the test devices can detect the presence of glucose, ketone bodies, cholesterol, triglycerides, bilirubin, urobilinogen, occult blood, nitrite, protein, urea, potassium, and other substances. A specific change in the intensity of color observed within a specific time range after contacting the test device with a sample, is indicative of the presence of a particular analyte and of the concentration of the analyte in the sample.

It is customary for reagent test devices to contain more than one test reagent-containing bibulous matrix, such that each test reagent-containing bibulous matrix is capable of detecting a particular analyte in a liquid test sample. For example, a diagnostic device could contain a test reagent-containing bibulous matrix responsive to glucose in urine and another bibulous matrix responsive to ketones, like acetoacetate, such that the second bibulous matrix is spaced from, but adjacent to, the glucose-responsive bibulous matrix. One diagnostic test device for urine contains eight adjacent test reagent-containing bibulous matrices providing analytical measurement of pH, protein, glucose, ketones, bilirubin, occult blood, nitrite, and urobilinogen.

For some assays, such as those performed on whole blood, it has been found that the normal method of simply dipping the diagnostic device into the liquid sample cannot be used. For such assays the amount or volume of the test sample contacting the test-reagent containing diagnostic device is very critical. For example, dry reagent methods for testing whole blood or serum require the application of specific test sample volumes and the use of sophisticated filtering and separating techniques to obtain accurate results.

Therefore, in order to achieve accurate and reproducible results, a very precise amount of sample must contact the test-reagent containing bibulous matrix each time an assay is performed. For these assays in particular, the development of a volume independent diagnostic device, wherein a precise and reproducible amount of test sample contacts the test reagent-containing bibulous matrix each time an assay is performed, would be extremely advantageous. Such a device would overcome the problems of inaccurate and inconsistent results due to differences in the amount of test sample contacting the test reagent in the bibulous matrix. The method and device of the present invention is primarily directed at providing a constant sample loading of test sample per unit volume of a test reagent-containing bibulous matrix, and as a result, a truly volume independent diagnostic device.

Other considerations also arise in developing a process and device for testing liquids for a specific analyte. One important consideration is the gross sample size needed to perform the analyte determination. For instance, in testing whole blood, an ideal process includes withdrawing a whole blood sample in "noninvasive" amounts, such as a pin prick drop, and immediately depositing the undiluted whole blood sample on the diagnostic device.

Another consideration is the degree of sophistication of the technician performing the assay. It is often desirable to have relatively untrained personnel carry out routine assays and obtain accurate quantitative results. In these situations, it is important that the assay method contain a minimum of manipulative steps, be free of possible interferences or contamination and provide for easy measurement. For instance, among the several possible manipulative steps, testing the incorrect sample or applying the incorrect amount of sample to the diagnostic device are the most probable areas of assay error.

Therefore, a need exists for a process and device for rapidly and accurately testing a small volume of liquid for a particular analyte, wherein accurate and reproducible analyte concentrations are obtained independent of sample size. Such a method and device for determining analyte concentrations in liquids would allow medical personnel to carry out analyte assays on a more routine and more confident basis.

The "dip-and-read" method for testing urine samples has enjoyed great success due to the ease, speed and low cost of testing liquid samples. However, substantial work is still being performed in this area as diagnostic device uses are demanding more accurate test methods, for more analytes, on smaller liquid test samples. Diagnostic device users are especially eager to reduce the possibility of test inaccuracy, usually by making the test method simpler and less operator dependent. The ideal way to reduce operator dependence is to eliminate the need to dilute the liquid test sample and to eliminate the need to introduce a precise sample volume to the diagnostic device. It is to the latter objective that the method and device of the present invention is directed.

Indicative of the work conducted in this field is U.S. Pat. No. 3,798,004 to Zerachia et al, disclosing a semiquantitative method for determining analyte concentrations with a laminated device including a reagent-impregnated matrix placed between a pair of liquid impervious members. The analyte-containing sample contacts the reagent-impregnated matrix along the matrix-exposed edge of the test device. As the analyte-containing sample progresses inwardly towards the center of the matrix, the analyte reacts with the reagent impregnated in the matrix to provide a visible color pattern. The depth of the inward penetration of the color pattern is measured to determine the concentration of the analyte in the test solution. The amount of test sample absorbed by the matrix is limited by the capacity of the matrix to hold liquids, so a semiquantitative determination of an analyte is possible.

Similarly, Morison in U.S. Pat. No. 3,620,677 describes an indicating device including an impervious material encasing a reagent-treated capillary material, such that at least some of the capillary material is exposed. The analyte-containing sample is applied to the capillary material, and, as the sample chromatographs through the reagent-treated capillary material, a chromogenic reaction occurs. After complete analyte reaction, the chromogenic reaction ceases. Therefore the point that the color formation ends gives a reading of the approximate analyte concentration. The method disclosed in the Morison patent is volume dependent, as the amount of analyte, and therefore the degree of the chromogenic reaction, increases with sample volume.

Nussbaum in U.S. Pat. No. 3,810,739 discloses a reagent-impregnated paper encased in a plastic covering, so arranged such that a test sample can be introduced only through a single opening. A chromogenic reaction occurs within the device, and is observed through the translucent plastic used to encase the reagent-impregnated paper. The method and device of the Nussbaum patent are directed to qualitatively determining the presence or absence of a particular chemical or bacterial constituent of a solid or liquid sample. The device is constructed to retard sample evaporation during periods of long reaction incubation, especially at high temperatures. As a result, the volume or weight of test sample is an unimportant variable in the method disclosed in the Nussbaum patent.

U.S. Pat. No. 4,069,017 to Wu et al discloses contacting adjacent matrices in order to provide uniform distribution of a test sample from a first, untreated matrix to a second, reagent-impregnated matrix. Although the device does reduce volume dependence, the configuration of the matrices is specifically designed to provide a uniform bilirubin distribution to the reagent-impregnated matrix for uniform binding and chromogenic reaction.

Kondo et al U.S. Pat. No. 4,256,693 discloses a multilayered device including a layer to remove insoluble constituents, a waterproof layer with an opening, a porous spreading layer and a reagent layer, in that order. This device delivers a less-than-saturating volume of test sample from the spreading layer to the reagent layer as a method to ensure even sample distribution. Accordingly, the spreading layer does not and could not act as a barrier layer.

U.K. Pat. No. 2,090,549 discloses an analytical device for metering a precise quantity of blood utilizing a metering channel. Capillary action draws only a certain amount of blood into the metering channel for distribution through a filter layer to a layer impregnated with a reagent.

U.S. Pat. No. 4,647,430 discloses a volume independent test device wherein a reagent-impregnated matrix is completely covered by a microporous film. A liquid sample penetrates the film until the matrix is saturated, resulting in a constant loading of sample per unit area.

SUMMARY OF THE INVENTION

In brief, the present invention is directed to a process and device for quantitatively determining analyte concentrations in liquids, whereby assay sensitivity to sample volume is essentially eliminated. It has been found that the method and device of the present invention unexpectedly give accurate and reproducible analyte determinations from small, but variable, test sample volumes by consistently metering a precise amount of the test sample to an assay area of the device.

According to the method of the present invention, an excess sample amount of the analyte-containing liquid is applied to a diagnostic device comprising a first bibulous matrix that is adjacent to, and in contact with, a second bibulous matrix. The second bibulous matrix has been treated with a reagent suitable for detecting a specific analyte. In addition, the reagent-treated second bibulous matrix and a portion of the untreated first matrix are covered with a liquid-impermeable coating or film. The impermeable coating or film serves to assist in metering the liquid sample into the first and second bibulous matrices and to act as a barrier to prohibit the test sample from directly contacting the reagent-treated bibulous matrix. From an area of liquid test sample addition, the sample is directed to the reagent-treated area of the second bibulous matrix by the wicking action of the matrix until the matrices are saturated with liquid.

The method and device of the present invention are ideally suited for quantitative analyte determinations that are sensitive to test sample volume. By the method of the present invention, the liquid-impermeable coating or film meters the test sample into the bibulous matrices. The liquid-impermeable coating or film covering the reagent-impregnated bibulous matrix also prohibits excess test sample from entering the assay area of the device. The liquid test sample is directed to the test reagent-treated assay area of the bibulous matrix by the wicking action of the bibulous matrix from the area of sample application. The reagent-treated assay area of the matrices absorbs liquid test sample only up to the point of matrix saturation, thereby providing a specific volume of liquid test sample for analyte determination from an initially variable volume of applied liquid test sample.

More particularly, in accordance with the present invention, the device includes one or more hydrophilic bibulous matrices securely adhered to a hydrophobic substrate. At least one of the bibulous matrices, or, in another embodiment, at least a portion of the single bibulous matrix, is treated with a sufficient amount of a test reagent suitable to test for a specific analyte. As used herein, the expression "test reagent" is defined as a chemical or mixture of chemicals causing an observable or detectable reaction when contacted with the substance being detected. The test reagent-treated bibulous matrix, or test-reagent treated portion of the bibulous matrix, is laminated with a liquid-impermeable coating or film to act as a barrier and prohibit the test sample from directly contacting the test reagent-treated matrix. The excess test sample is applied to the uncovered portion of the bibulous matrix or matrices. The bibulous matrix or matrices absorbs the test sample, and the sample is metered by capillary action to the test reagent-treated matrix or matrices located beneath the liquid-impermeable coating or film. After the test sample saturates the bibulous matrices, no further liquid sample enters the aatrices, thereby making the method and device essentially volume independent. If the technician inadvertently applies some of the liquid test sample to the top surface of the liquid-impervious coating or film, after the liquid test sample saturates the bibulous matrix or matrices, any excess liquid test sample is wiped away from the top surface of the coating or film before quantitative analyte determination.

In accordance with an important feature of the present invention, the test sample passes chromatographically to an assay area of the same, or an adjacent, bibulous matrix, containing a suitable test reagent, to perform the assay of interest. The test sample reacts or interacts with the test reagent in the assay region to produce a detectable change in the assay region, such as a color change, to chromogenically indicate the presence or absence of a particular analyte and/or to allow quantitative determination of the particular analyte.

Therefore, the present invention is directed to a method and device for rapidly and effectively determining the presence and concentration of a particular analyte, independent of the test sample volume applied to the device More particularly, in accordance with another important feature of the present invention, one or more test reagent-treated, hydrophilic bibulous matrices are so arranged such that a precise and reproducible volume of a liquid test sample is metered to the test-reagent treated bibulous matrix for qualitative or quantitative determination of a particular analyte.

According to the method of the present invention, an excess amount of test sample is deposited on the area of the bibulous matrix that is not covered by the liquid-impervious coating or film. The test sample, metered into the bibulous matrices by the liquid-impervious coating or film, passes chromatographically through the bibulous matrix to the assay area of the same bibulous matrix, or to the assay area of a second, adjacent bibulous matrix. In either case, the assay area has been previously treated to include a test reagent such that the particular analyte of interest can be detected immediately without any further manipulative steps such as dilution. In addition, covering the assay area of the bibulous matrices with a liquid-impermeable coating or film precludes immediate contact of the test sample with the test reagent-treated matrix. Therefore, a precise amount of test sample, essentially independent of the initial volume of test sample applied to the test device, is metered to the assay area and the excess test sample does not contaminate the assay area.

In general, the amount of test sample applied to the exposed surface of the bibulous matrix is unimportant. The test sample deposited on the exposed area of the bibulous matrix is metered to the test reagent-treated matrix until the bibulous matrix is saturated with liquid. After matrix saturation, any liquid test sample contacting the top of the liquid-impermeable coating or film is removed before quantitative analyte determination. The excess test sample is prevented from reacting with, or contaminating, the test reagent in the test reagent-treated bibulous matrix by the liquid-impermeable film or coating.

According to the method of the present invention, the liquid-impermeable film or coating and the bibulous matrix or matrices allow an excess amount of test sample to be applied to the diagnostic device. The exposed bibulous matrix will chromatograph, or meter, a precise amount of test sample to the assay area. The amount of test sample introduced into the assay area will depend upon the size and absorptivity of the particular bibulous matrix of the device. Accordingly, the resulting diagnostic device achieves constant loading of test sample per unit volume of bibulous matrix independent of the amount of sample applied to the diagnostic device, thereby producing a volume independent diagnostic device.

The method and device of the present invention are ideally suited for performing a broad range of volume sensitive analyte determinations that are conducted primarily on bibulous matrices such as paper. These analyte determinations include assays for triglycerides, galactose, glucose, potassium ions, AST, cholesterol, creatinine, ALT, phenobarbital, bilirubin, theophylline, urea, dye samples and other immunochemical assays.

Therefore, it is an object of the present invention to provide a method and device for determining analyte concentrations in liquid samples quickly, effectively and accurately.

It is also an object of the present invention to provide a method and device for the rapid, convenient and effective analysis of analyte concentrations in small liquid samples.

Another object of the present invention is to provide a method and device for determining analyte concentrations in liquids that is independent of sample volume applied to the device.

Another object of the present invention is to provide a method and device that delivers a constant and reproducible amount of analyte-containing liquid to an assay area of the device, independent of the amount of excess sample applied to the device.

Another object of the present invention is to provide a method and device to determine analyte concentrations in small liquid samples with a minimum of manipulative steps.

Another object of the present invention is to provide a method and device to test small liquid samples for analytes wherein the nature and the amount of the analytes are not altered by the device prior to contacting the test-reagent treated bibulous matrix.

BRIEF DESCRIPTION OF THE DRAWING

The above and other objects and advantages of the present invention will become apparent from the following detailed description of the present invention taken in conjunction with the drawings, wherein.

DETAILED DESCRIPTION OF THE INVENTION

Figure 1:
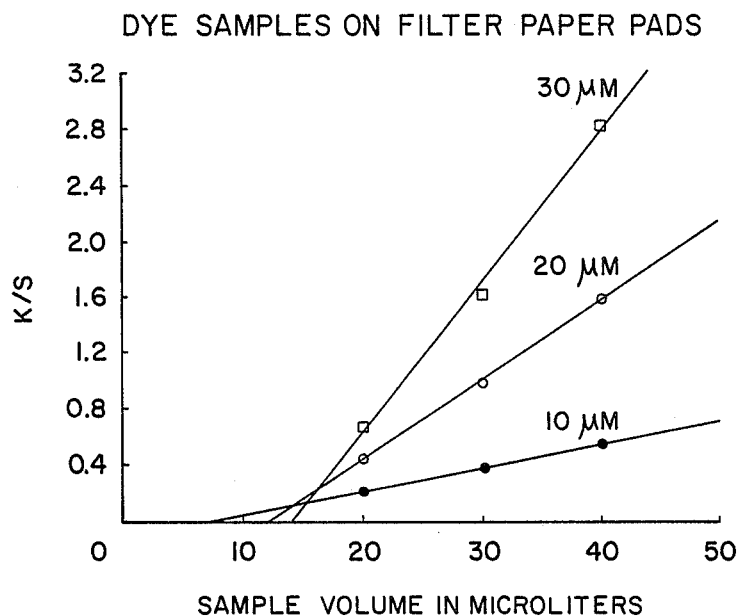
FIGS. 1 through 20 are graphs showing the volume dependence of several different diagnostic test device configurations by plotting the Kubelka-Munk function (K/S) versus the volume of test solutions added to the diagnostic device.

In accordance with the present invention, accurate and reproducible quantitative analyte determinations can be performed on liquid samples, such that the assay results are essentially independent of the test sample volume applied to the diagnostic device. According to the method and device of the present invention, a small liquid sample, such as a pinprick amount, is sufficient for quantitative analyte determinations, as opposed to the relatively large volume test samples required in the typical dip-and-test method of analyte determination. Unexpectedly, the device of the present invention, after the introduction of an excess amount of the test sample, meters a precise and constant amount of test sample to a test reagent-treated bibulous matrix. The test sample then is assayed for a particular analyte within minutes without any additional manipulative steps Surprisingly, the process and device of the present invention provide rapid, economical and accurate quantitative analyte determinations on liquid test samples without having to add a predetermined and precise amount of test sample to the diagnostic device. Overall, the process and device of the present invention are ideally suited for routine analyte determinations in small laboratories or private physician offices, wherein the number of assays may be relatively low, but accurate results are still required within a short time period.

As will become apparent, the method and device of the present invention are especially suited for analyte determinations utilizing chromogenic or other visual responses to test for the presence, absence or concentration of various analytes in liquid test samples For quantitative analyte determinations, it is of primary importance that a known, constant amount of test sample reach the assay area of the diagnostic device in order for the chromogenic reaction to be detected and accurately measured. For example, presently used diagnostic test devices are not only sensitive to the concentration of the analyte of interest, but are also sensitive to the volume of test sample applied to the diagnostic device. Table I illustrates the affect of sample volume size upon various quantitative analyte determinations made on whole blood. For example, for each 1% change in sample volume, the quantitative assay of AST will change by 0.3%.

TABLE I

VOLUME DEPENDENCY OF ANALYTE DETERMINATIONS

| Analyte | Volume Dependence (% Change in Assay for a 1% Change in Sample Volume) |
| --- | --- |
| AST | 0.3 |
| Creatinine | 0 to 0.5 |
| Cholesterol | 1.3 |
| Triglycerides | 1.0 |
| Potassium | 0.1 |
| Dye Samples | 1.0 |

In accordance with the present invention, it has been found that sample volume independence in analyte determinations of liquid samples is attained by metering the liquid test sample into one or more bibulous matrices. The test sample, as it is metered to the bibulous matrix, chromatographs through the bibulous matrix by wicking action until the matrix is saturated with test sample. After the bibulous matrix is saturated by the liquid, no further test sample enters the matrix.

According to the method and device of present invention, the bibulous matrices absorb liquid only up to the point of matrix saturation. Thus, since no liquid enters the bibulous matrix after saturation, the device of the present invention is essentially volume independent, giving accurate and reproducible analyte determinations regardless of the volume of test sample applied to the device.

Generally, the bibulous matrix of the present invention can be any hydrophilic, absorbent matrix that is amenable to treatment with a test reagent. The bibulous matrix also should permit the test sample to uniformly chromatograph through the matrix by wicking action at such a rate as to allow rapid analyte determinations. In addition, the bibulous matrix should not contaminate the test sample by test sample extraction of components of the bibulous matrix, by removing test sample constituents through chemical or physical interactions, or by appreciably altering the test sample in a way to make the subsequent analyte assays inconclusive, inaccurate or doubtful.

The bibulous matrix of the present invention is a hydrophilic material, possessing the above-mentioned characteristics, that allows the test sample to move chromatographically, in response to capillary forces, through the matrix. The test sample migrates essentially unchanged through the bibulous matrix to an assay area of the device and is retained by the bibulous matrix.

The bibulous matrix can be any hydrophilic material that allows the test sample to pass through the matrix to contact the assay area for analysis. Suitable bibulous matrices include hydrophilic inorganic powders, such as silica gel, alumina, diatomaceous earth and the like; sponge materials; glass fibers; argillaceous substances, cloth, hydrophilic natural polymeric materials, particularly cellulosic material, like cellulosic beads, and especially fiber-containing papers such as filter paper or chromatographic paper, synthetic or modified naturally-occurring polymers, such as nitrocellulose, cellulose acetate, polyvinyl chloride, polyacrylamide, polyacrylates, polyurethanes, crosslinked dextran, agarose, and other such crosslinked and noncrosslinked water-insoluble hydrophilic polymers. Hydrophobic substances, such as a hard, porous plastic, are not suitable for use as the bibulous matrix of the present invention.

The bibulous matrices included in a device of the present invention can have different physical characteristics and can be of different chemical compositions or a mixture of chemical compositions. The matrices can also vary in regards to smoothness and roughness combined with hardness and softness. However, in every instance, the bibulous matrix must include a hydrophilic material. Regardless of the exact composition of the bibulous matrix, the primary considerations are absorbency, wicking action and transmittal of substantially unaltered test samples.

In accordance with an important feature of the present invention, the hydrophilic, bibulous matrix includes a cellulosic material, such as paper, and preferably a fiber-containing paper, such as filter paper. Filter paper possesses all of the qualities required of a bibulous matrix of the present invention, plus the advantages of abundant supply, favorable economics, and a variety of suitable grades. Such paper has been found to be extremely satisfactory for use as a matrix material for suspending, transmitting and positioning both the test reagent and the test sample. Filter paper has been found to have particular utility in retaining the testing reagent, and in chromatographing the test sample by wicking action to the assay area. As known to those skilled in the art of basic chemistry, filter paper can be obtained in a variety of thicknesses and porosities. Since the method of the present invention requires the test sample to be metered into the bibulous matrix and subsequently chromatographed to the assay area of the bibulous matrix, it is well within the experimental techniques used by those skilled in the art of preparing test devices to determine the proper balance between bibulous matrix size, thickness and porosity in relation to concentration of test reagent.

To achieve the full advantage of the present invention, the bibulous matrix is in the form of a pad, having dimensions of, for example, approximately 0.25 cm by 0.5 cm to 0.5 cm by 1 cm. A pad of these dimensions allows an excess amount of test sample, applied at one end of the pad, to chromatograph through the pad to the assay area of the device within a reasonably short time. Increasing the size of the bibulous matrix substantially increases the time of analyte determination, and also requires a larger test sample.

In one embodiment of the present invention, the first bibulous matrix, after appropriate sizing, e.g., 0.5 cm×0.5 cm, is secured to a transparent or opaque, hydrophobic plastic handle. Then, immediately adjacent to and in contact with the first bibulous matrix, a second bibulous matrix, containing the test reagent necessary to assay for a particular analyte, is secured to the hydrophobic handle. The liquid-impervious coating or film then is laminated over the second bibulous matrix and, optionally, over a portion of the first bibulous matrix.

In accordance with an important feature of the present invention, the liquid impervious film or coating allows only that volume of liquid test sample sufficient to saturate the matrices to enter the bibulous matrices. The liquid impervious film or coating prohibits excess liquid test sample from entering the bibulous matrices, and thereby making the method and device volume independent. It has been found that by applying an excess amount of liquid test sample to a bibulous matrix of a diagnostic device having two contacting, adjacent bibulous matrices, lacking a covering layer of liquid impervious film or coating, results in an excess amount of liquid test sample entering the second bibulous matrix. The excess sample amount was observed as a free liquid collecting on the top surface of the second bibulous matrix. According to the method and device of the present invention, and as will be discussed more fully hereinafter, the liquid impermeable film or coating covering the two bibulous matrices prevents any excess liquid test sample from entering the second bibulous matrix.

At the present time, reagent-strip test formats utilize a test-reagent treated bibulous matrix, whereby a fixed volume of test sample is applied to the reagent test strip, and the reflectance is measured at a fixed time or series of times. In using this format, if the volume of test sample varies, the quantitative determination of analyte varies. Therefore, to illustrate the new and unexpected results of the method and device of the present invention, several methods for reducing analyte determination dependence upon test sample volume were compared. More specifically, the methods included applying test samples to each of the following test devices:

0. The standard control format, utilizing a single test reagent-treated bibulous matrix, with the test sample applied directly to the test area.

1. The film cover format, wherein an untreated bibulous matrix is placed adjacent to and in contact with a second test reagent-treated bibulous matrix. The test-reagent treated matrix is covered completely by a clear, liquid impervious coating or film. The test sample is applied to the uncovered and untreated bibulous matrix and chromatographs through the untreated bibulous matrix to the reagent-treated bibulous matrix. After saturation, no further sample enters the bibulous matrices and any excess sample then is removed.

2. The touch off format, wherein a single test-reagent treated bibulous matrix is utilized as in control format 0. A liquid test sample is applied to the single test-reagent treated bibulous matrix, then excess sample is removed from the bibulous matrix by contacting the matrix with a dry piece of filter paper and allowing the excess sample to wick from the bibulous matrix.

3. Blot lightly format, wherein a test sample is applied to a single test-reagent treated bibulous matrix (format 0), then the excess sample is removed by blotting lightly with a dry piece of filter paper.

4. Blot heavily format, wherein a test sample is applied to a single test-reagent treated bibulous matrix (format 0), then the excess sample is removed by blotting heavily with a dry piece of filter paper.

5. Adjacent dry pad format, wherein an untreated bibulous matrix is placed adjacent to and in contact with a second test reagent-treated bibulous matrix A test sample is applied to the test reagent-treated bibulous matrix, and the untreated bibulous matrix wicks off the excess test sample from the test reagent-treated bibulous matrix.

6. Adjacent dry pad with bridge format, wherein an untreated bibulous matrix is placed next to a second test-reagent treated bibulous matrix, but separated from the second matrix by a distance of 1 to 2 mm. A thin bridge of tissue paper connects the two bibulous matrices. The test sample is applied to the test reagent-treated bibulous matrix, and excess sample can wick to the untreated bibulous matrix through the tissue paper bridge.

7. Apply to adjacent pad format, wherein an untreated bibulous matrix is placed adjacent to and in contact with a second test-reagent treated bibulous matrix as in format 5, however, the test sample is applied to the untreated bibulous matrix.

8. Apply to adjacent pad with bridge format, wherein the test device is prepared as in format 6, however, the test sample is applied to the untreated bibulous matrix and wicks through the tissue paper bridge to the test reagent-treated bibulous matrix.

9. Dip reagent format, utilizing the standard control format (format 0), except the test device is dipped into the test sample, as opposed to applying the test sample to the test device.

The volume dependence of the above-described test devices was determined by applying dye solutions to test devices having untreated filter paper as the bibulous matrices and/or by applying analyte calibrator solutions to test devices having bibulous matrices treated with the appropriate test reagent for that particular analyte solution. Individual test results were determined by taking a reflectance measurement with a reflectance photometer at a suitable time and wavelength for that particular analyte determination. The reflectance, as taken from the reflectance scale of zero to one, was incorporated into the Kubelka-Munk function:

$$K/S = (1-R)^2/2R,$$

wherein K is the absorption coefficient, S is the scattering coefficient and R is reflectance. In FIGS. 1 through 20, the K/S values were plotted against the volume of liquid test sample applied to the test device. Generally, it can be stated that as reflectance decreases, the K/S value increases.

For example, FIG. 1 shows three graphs of K/S values versus sample volume. Each graph shows the effect of adding increased dye sample to a diagnostic device having untreated bibulous matrices made of filter paper and arranged in the standard control format (0). Three separate dye solutions, having dye concentrations of $1 \times 10^{-5}$ M, $2 \times 10^{-5}$ M and $3 \times 10^{-5}$ M, were used. The graphs plotted in FIG. 1 illustrate the data tabulated in Example 1. In Example 1, each test was run in duplicate, using two instruments. The dye solutions were applied to untreated filter paper matrices, and the reflectance was measured at a wavelength of 630 nm (nanometers). The tabulated K/S values are given as duplicate pairs of the average K/S values for three replicate trials. The standard deviation over the replicate trials is also tabulated. Examples 2 through 28 include similarly conducted tests, with similarly tabulated test results.

EXAMPLE 1

Dye Solution Applied to Untreated Filter Paper—Standard Control Format (0)

FIG. 1: Tests performed in duplicate, using two instruments, two 0.5×0.5 cm filter paper matrices, wavelength—630 nm.

| VOLUME OF DYE SOLUTION APPLIED TO TEST DEVICE | CONCENTRATION OF DYE SOLUTION | | | | | |
|---|---|---|---|---|---|---|
| | $1 \times 10^{-5}$ M | | $2 \times 10^{-5}$ M | | $3 \times 10^{-5}$ M | |
| | K/S | STD. DEVIATION | K/S | STD. DEVIATION | K/S | STD. DEVIATION |
| 20 uL | 0.208 | 0.003 | 0.465 | 0.011 | 0.689 | 0.046 |
| | 0.198 | 0.006 | 0.443 | 0.017 | 0.670 | 0.023 |
| 30 uL | 0.417 | 0.022 | 1.043 | 0.053 | 1.619 | 0.142 |
| | 0.381 | 0.011 | 0.936 | 0.070 | 1.620 | 0.255 |
| 40 uL | 0.542 | 0.005 | 1.559 | 0.028 | 2.754 | 0.061 |
| | 0.540 | 0.012 | 1.633 | 0.098 | 2.896 | 0.201 |

EXAMPLE 2

Cholesterol Solution Applied to Treated Filter Paper—Standard Control Format (0)

Figure 2:
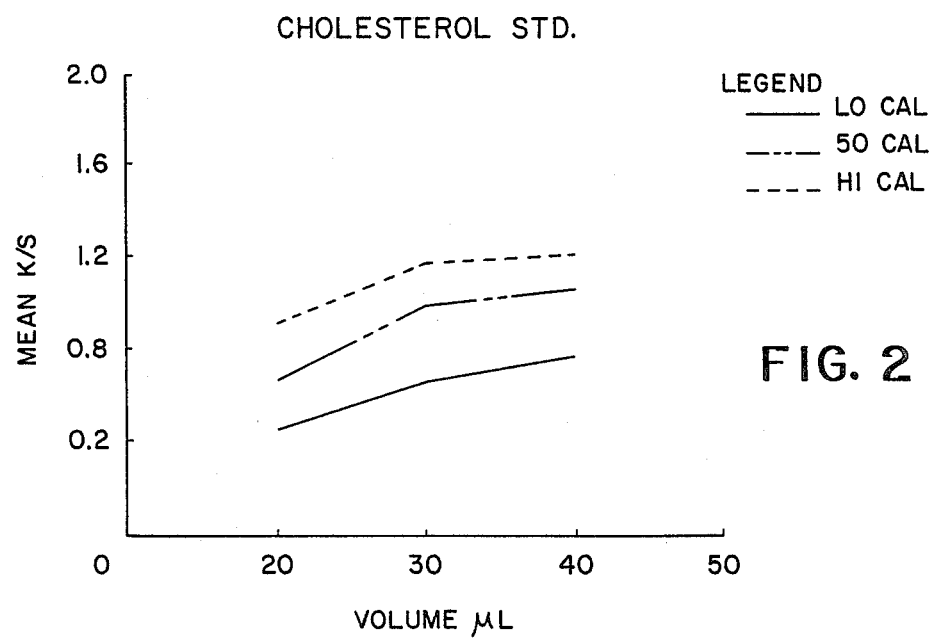

FIG. 2: Data obtained as in Example 1, using appropriate commercial test reagent and wavelength—600 nm.

| VOLUME OF CHOLESTEROL SOLUTION APPLIED TO TEST DEVICE | CONCENTRATION OF CHOLESTEROL SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 20 uL | 0.450 | 0.006 | 0.663 | 0.003 | 0.910 | 0.025 |
| 30 uL | 0.656 | 0.017 | 0.993 | 0.024 | 1.173 | 0.079 |
| 40 uL | 0.768 | 0.033 | 1.067 | 0.039 | 1.205 | 0.051 |

EXAMPLE 3

Triglyceride Solution Applied to Treated Filter paper—Standard Control Format (0)

Figure 3:
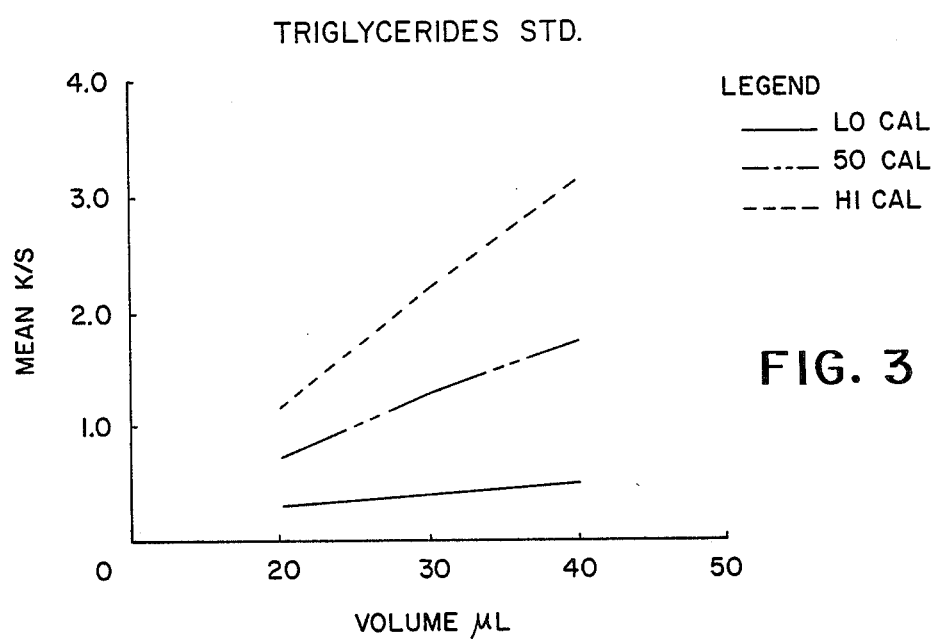

FIG. 3: Data obtained as in Example 1, using appropriate commercial test reagent and wavelength—580 nm.

| VOLUME OF TRIGLYCERIDE SOLUTION APPLIED TO TEST DEVICE | CONCENTRATION OF TRIGLYCERIDE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 20 uL | 0.301 | 0.007 | 0.723 | 0.013 | 1.146 | 0.042 |

| VOLUME OF TRIGLYCERIDE SOLUTION APPLIED TO TEST DEVICE | CONCENTRATION OF TRIGLYCERIDE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.404 | 0.020 | 1.286 | 0.025 | 2.176 | 0.080 |
| 40 uL | 0.512 | 0.007 | 1.742 | 0.016 | 3.132 | 0.070 |

EXAMPLE 4

Potassium Ion Solution Applied to Treated Filter Paper—Standard Control Format (0)

Figure 4:
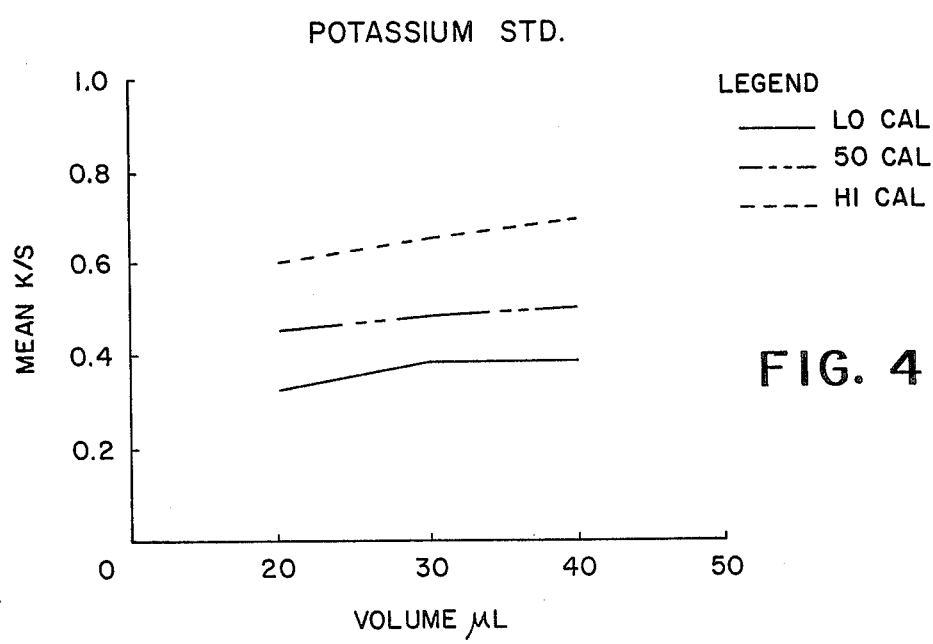

FIG. 4: Data obtained as in Example 1, using appropirate commercial test regent and wavelength—640 nm.

| VOLUME OF POTASSIUM ION SOLUTION APPLIED TO TEST DEVICE | CONCENTRATION OF POTASSIUM ION SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 20 uL | 0.325 | 0.007 | 0.450 | 0.012 | 0.603 | 0.009 |
| 30 uL | 0.378 | 0.005 | 0.475 | 0.017 | 0.653 | 0.014 |
| 40 uL | 0.380 | 0.016 | 0.501 | 0.008 | 0.693 | 0.017 |

EXAMPLE 5

Glucose Solution Applied to Treated Filter Paper—Standard Control Format (0)

Figure 5:
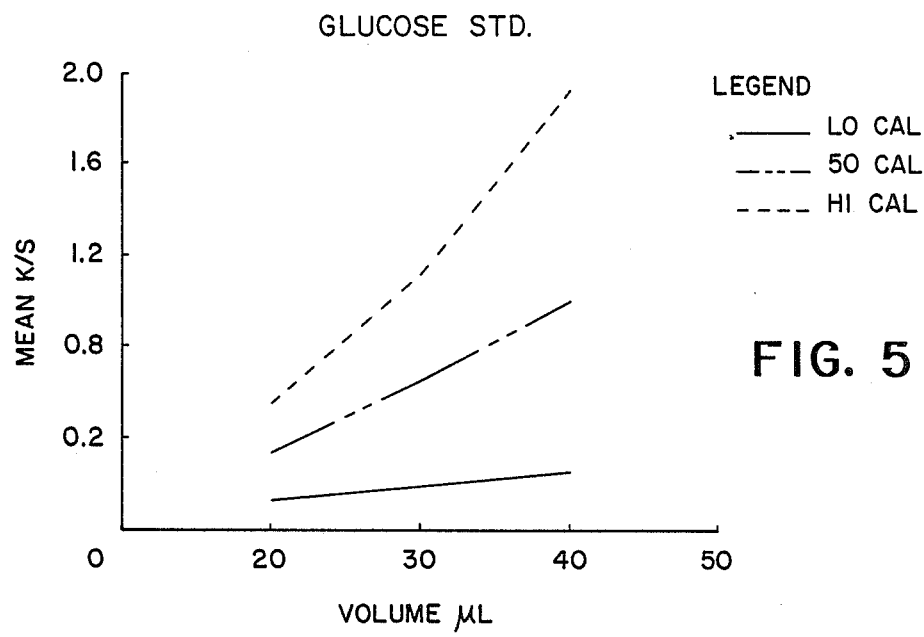

FIG. 5: data obtained as in Example 1, using appropriate commercial test reagent and wavelength—b 620 nm.

| VOLUME OF GLUCOSE SOLUTION APPLIED TO TEST DEVICE | CONCENTRATION OF GLUCOSE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 20 uL | 0.134 | 0.002 | 0.329 | 0.006 | 0.537 | 0.035 |
| 30 uL | 0.203 | 0.004 | 0.654 | 0.018 | 1.096 | 0.011 |
| 40 uL | 0.264 | 0.003 | 1.006 | 0.029 | 1.882 | 0.045 |

As shown in FIGS. 1 through 5, the dependence upon sample volume for test samples applied directly to devices having the standard control format (0) is quite large. The volume dependence is seen in the large slope of the graphed functions in FIGS. 1 through 5. Quantitatively, it has been found that the standard control format (0) gives a change of calculated concentration of analyte of approximately 1% for each 1% variation in sample volume. This large change in apparent analyte concentration shows a relatively large dependence upon sample volume, thereby necessitating the application of a precisely-measured test sample volume to test devices having the configuration of format (0).

Figure 6:
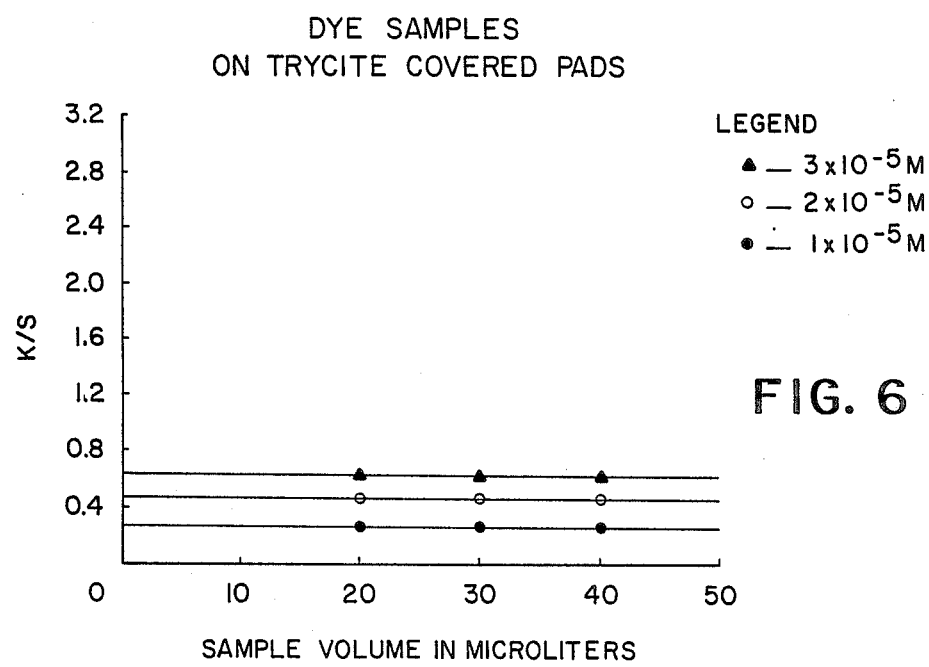

However, by applying varying volumes of a dye solution to a device of the present invention, the film cover format (1), no volume dependence in regard to applied test sample size is shown. FIG. 6 illustrates the K/S vs. test-sample volume data of Example 6. The slopes of the graphs shown in FIG. 6 are unexpectedly lower than the slopes of graphs of FIGS. 1 through 5 and, even more surprisingly the slopes of the graphs in FIG. 6 approach zero, thereby approaching a volume dependence of zero for a device having the film cover format (1).

EXAMPLE 6

Dye Solution Applied to Untreated Filter Paper—Film Cover Format (1)

FIG. 6: Tests performed in duplicate, using two instruments, two 0.5×1.0 cm. filter paper matrices, wavelength—630 nm.

| VOLUME OF DYE SOLUTION APPLIED TO TEST DEVICE | CONCENTRATION OF DYE SOLUTION | | | | | |
|---|---|---|---|---|---|---|
| | $1 \times 10^{-5}$ M | | $2 \times 10^{-5}$ M | | $3 \times 10^{-5}$ M | |
| | K/S | STD. DEVIATION | K/S | STD. DEVIATION | K/S | STD. DEVIATION |
| 40 uL | 0.270 | 0.004 | 0.473 | 0.015 | 0.639 | 0.022 |
| | 0.260 | 0.018 | 0.473 | 0.018 | 0.626 | 0.044 |
| 60 uL | 0.266 | 0.012 | 0.476 | 0.023 | 0.617 | 0.024 |
| | 0.269 | 0.005 | 0.475 | 0.007 | 0.608 | 0.035 |
| 80 uL | 0.258 | 0.004 | 0.444 | 0.006 | 0.607 | 0.033 |
| | 0.272 | 0.013 | 0.472 | 0.013 | 0.660 | 0.034 |

EXAMPLE 7

Cholesterol Solution Applied to Treated Filter Paper—Film Cover Format (1)

Data for Examples 7 and 8 was obtained as in Example 6, using the film cover format (1) and the appropiate test ereagent and wavelength for the particular analyte. Drops of the test sample were applied to the test device, however the volume of the drops of test sample applied to the test device was not quantitatively measured.

| VOLUME OF CHOLESTEROL SOLUTION APPLIED TO TEST DEVICE | CONCENTRATION OF CHOLESTEROL SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| Not Quantitatively Measured | 0.442 | 0.012 | 0.629 | 0.018 | 0.795 | 0.011 |
| | 0.454 | 0.022 | 0.699 | 0.030 | 0.855 | 0.042 |

EXAMPLE 8

Triglyceride Solution Applied to Treated Filter Paper—Film Cover Format (1)

| VOLUME OF TRIGLYCERIDE SOLUTION APPLIED TO TEST DEVICE | CONCENTRATION OF TRIGLYCERIDE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| Not Quantitatively Measured | 0.371 | 0.013 | 0.549 | 0.027 | 0.860 | 0.047 |
| | 0.384 | 0.005 | 0.618 | 0.030 | 0.888 | 0.042 |

In comparing the standard deviation values for the tests of Examples 1 through 5 to the standard deviation values for the tests of Examples 6 through 8, it is shown that the precision of the tests not precisely controlling the volume of test sample applied to the diagnostic device (Ex. 6–8) compare favorably to the tests performed utilizing the standard control format (0) and having a precise volume of test sample applied to the test device (Ex. 1–5).

EXAMPLE 9

Cholesterol Solution Applied to Treated Filter Paper—Touchoff Format (2)

Figure 7:
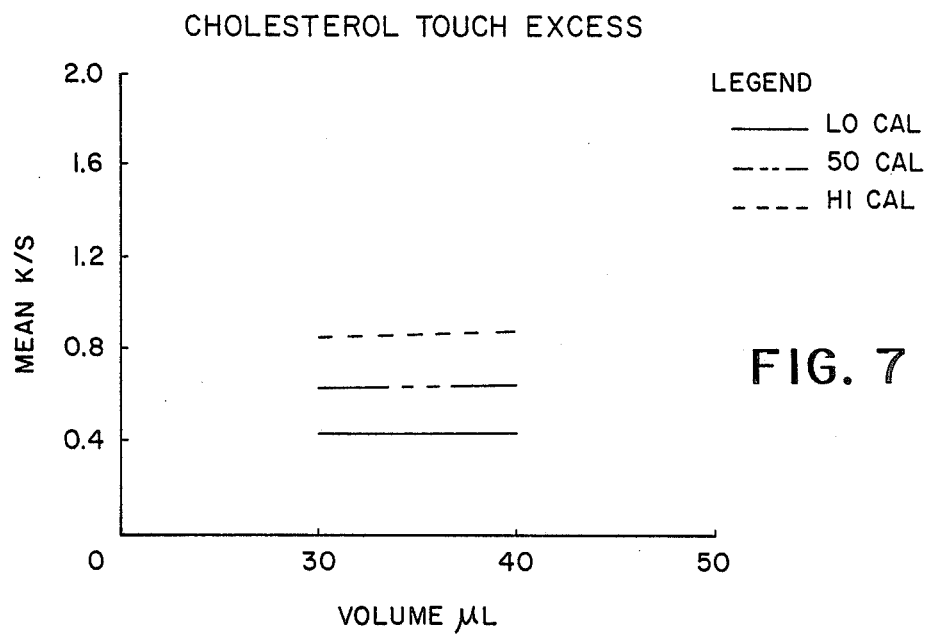

FIG. 7: Data obtained as in Example 2.

| VOLUME OF CHOLESTEROL SOLUTION APPLIED TO TEST DEVICE | CONCENTRATION OF CHOLESTEROL SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.429 | 0.018 | 0.633 | 0.033 | 0.846 | 0.058 |
| 40 uL | 0.438 | 0.007 | 0.639 | 0.012 | 0.876 | 0.009 |

EXAMPLE 10

Triglyceride Solution Applied to Treated Filter Paper—Touchoff Format (2)

Figure 8:
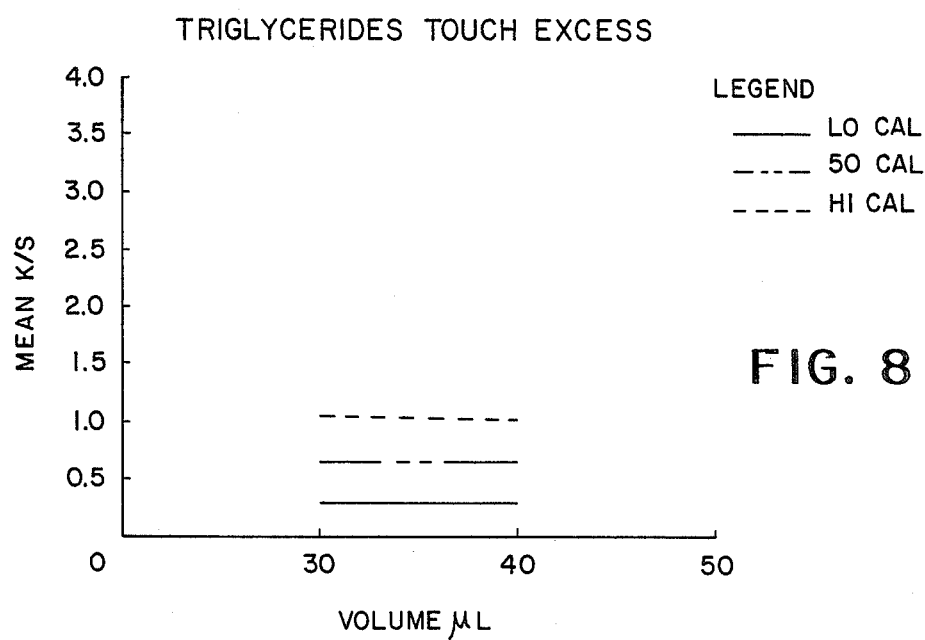

FIG. 8: Data obtained as in Example 3.

| VOLUME OF TRIGLYCERIDE SOLUTION APPLIED TO TEST DEVICE | CONCENTRATION OF TRIGLYCERIDE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.277 | 0.017 | 0.647 | 0.017 | 1.054 | 0.033 |
| 40 uL | 0.285 | 0.005 | 0.673 | 0.027 | 1.005 | 0.029 |

EXAMPLE 11

Potassium Ion Solution Applied to Treated Filter Paper—Touchoff Format (2)

Figure 9:
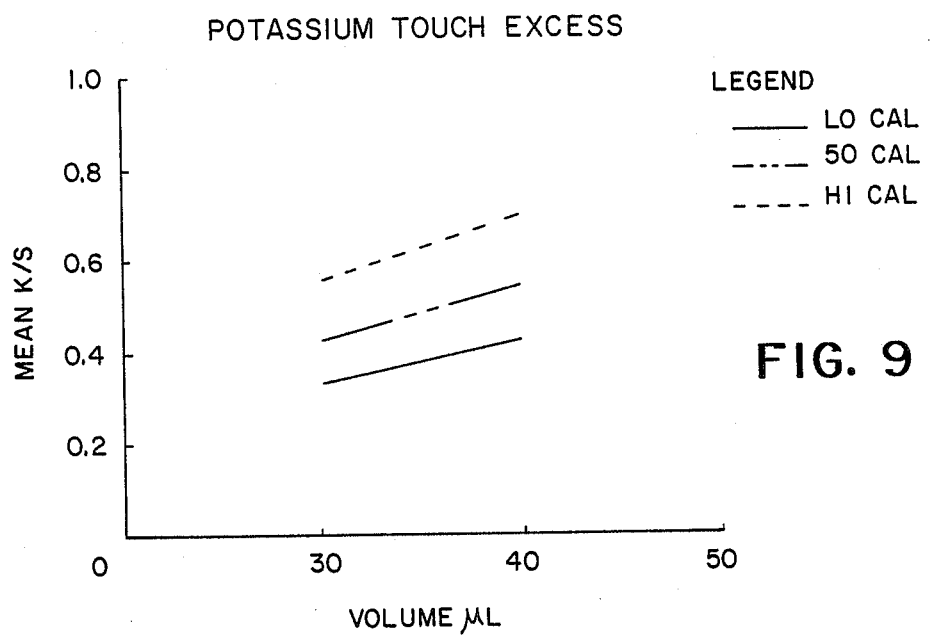

FIG. 9: Data obtained as in Example 4.

| VOLUME OF POTASSIUM ION SOLUTION APPLIED TO TEST DEVICE | CONCENTRATION OF POTASSIUM ION SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.330 | 0.002 | 0.418 | 0.005 | 0.546 | 0.024 |
| 40 uL | 0.417 | 0.004 | 0.535 | 0.006 | 0.691 | 0.008 |

EXAMPLE 12

Glucose Solution Applied to Treated Filter Paper—Touchoff Format (2)

Figure 10:
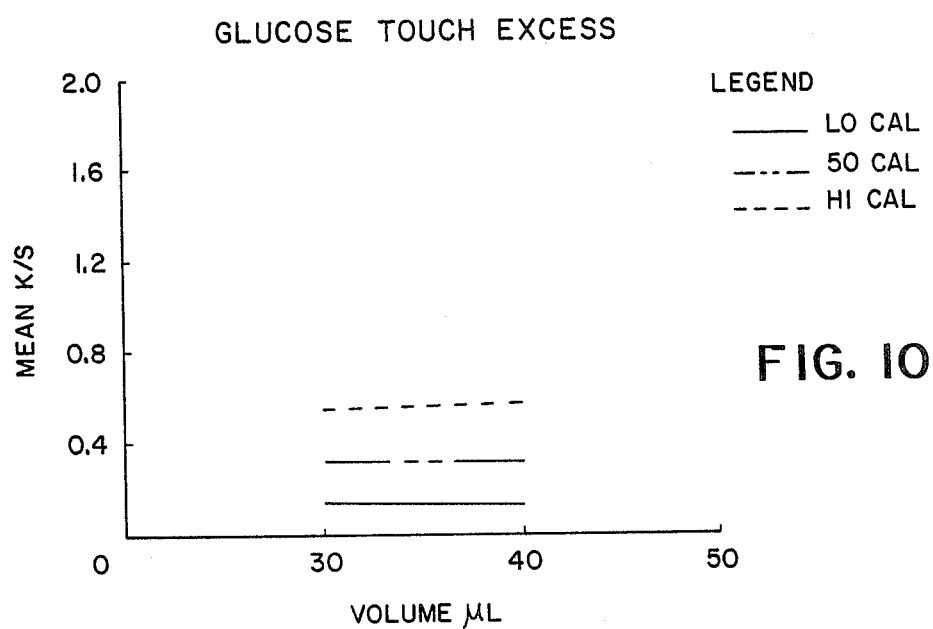

FIG. 10: Data obtained as in Example 5.

| VOLUME OF GLUCOSE SOLUTION APPLIED TO TEST DEVICE | CONCENTRATION OF GLUCOSE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.136 | 0.010 | 0.321 | 0.020 | 0.551 | 0.013 |
| 40 uL | 0.137 | 0.003 | 0.329 | 0.019 | 0.576 | 0.028 |

In Examples 9 through 12, a test sample volume of 20 microliters is approximately the saturation volume for the reagent-treated bibulous matrix. This volume of test sample does not provide excess test sample for removal, therefore 2-microliter test sample volumes were not tested. As shown by the slopes of the graphed function in FIGS. 8 through 10, a diagnostic device utilizing the touchoff format is relatively independent of applied test sample volume. However, this format has the disadvantages of being significantly dependent upon user technique and of requiring an additional manipulative step within the test.

EXAMPLE 13

Cholesterol Solution Applied to Treated Filter Paper—Blot Lightly Format (3)

Figure 11:
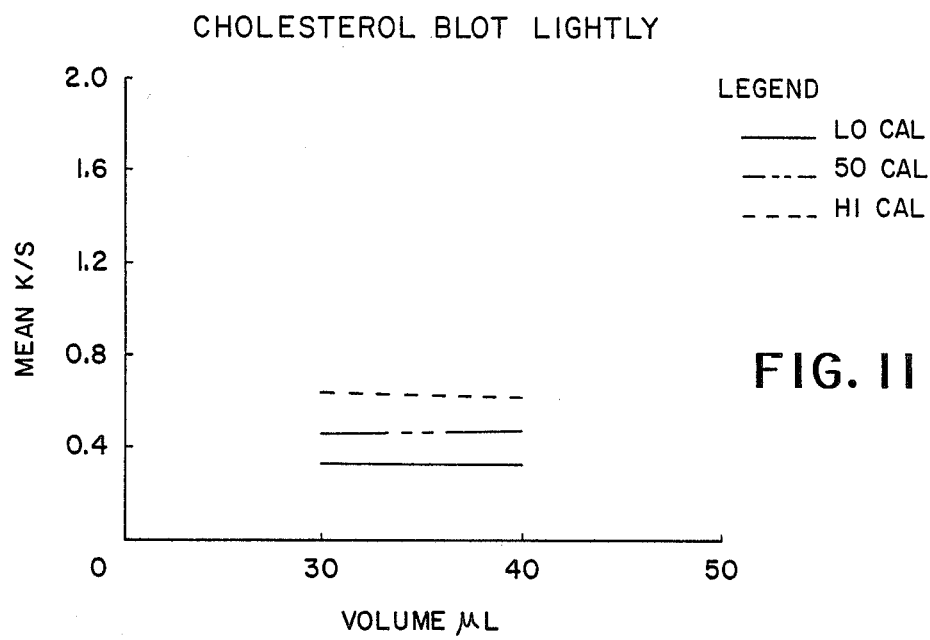

FIG. 11: Data obtained as in Example 2.

EXAMPLE 16

Glucose Solution Applied to Treated Filter Paper—Blot Lightly Format (3)

Figure 14:
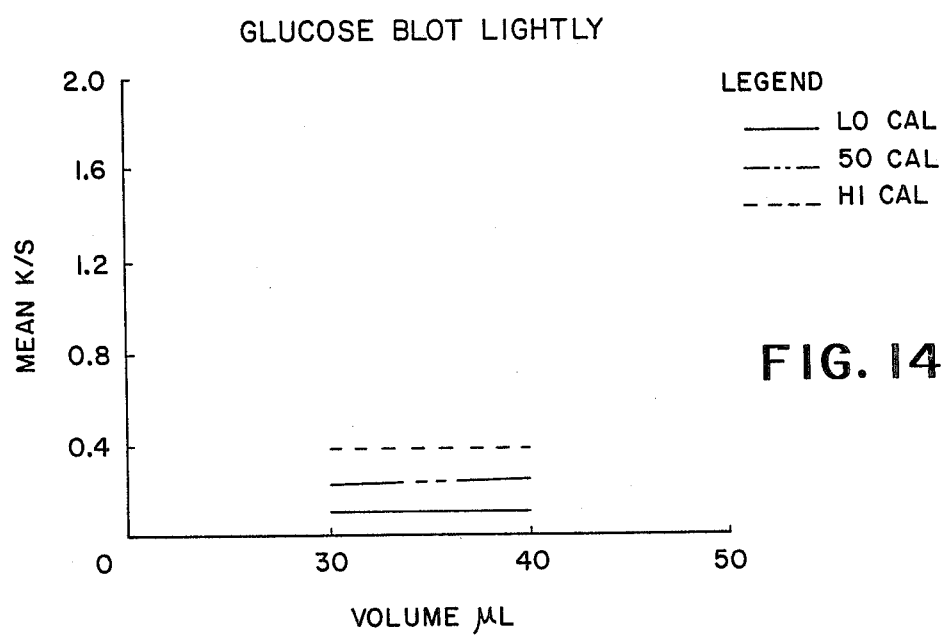

FIG. 14: Data obtained as in Example 5.

| VOLUME OF GLUCOSE SOLUTION APPLIED TO TEST DEVICE | CONCENTRATION OF GLUCOSE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.111 | 0.002 | 0.232 | 0.016 | 0.385 | 0.012 |
| 40 uL | 0.108 | 0.007 | 0.251 | 0.017 | 0.393 | 0.023 |

Examples 13 through 16 and FIGS. 11 through 14 show that the lightly blotting format does reduce the volume dependence compared to the standard control format (0), however, the blotting lightly formast (3) is highly dependent upon user technique. The volume independence of this format is highly dependent on the pressure of blotting, as can be seen by comparing Examples 13–16 to the following data obtained from the blotting heavily format (4).

| VOLUME OF CHOLESTEROL SOLUTION APPLIED TO TEST DEVICE | CONCENTRATION OF CHOLESTEROL SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.333 | 0.038 | 0.464 | 0.009 | 0.639 | 0.020 |
| 40 uL | 0.335 | 0.031 | 0.473 | 0.028 | 0.617 | 0.036 |

EXAMPLE 14

Triglyceride Solution Applied to Treated Filter Paper—Blot Lightly Format (3)

EXAMPLE 17

Cholesterol Solution Applied to Treated Filter Paper—Blot Heavily Format (4)

Figure 15:
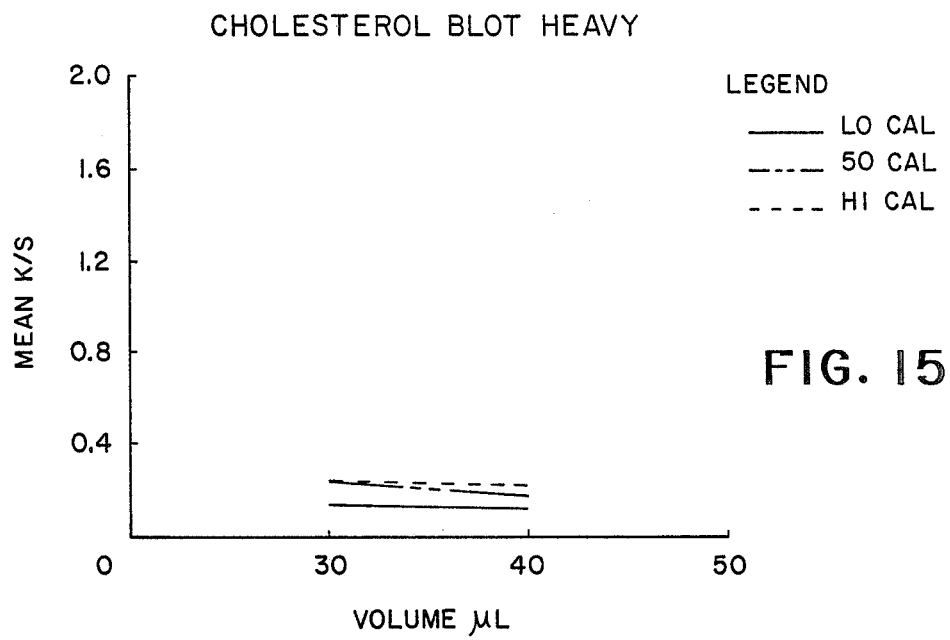

FIG. 15: Data obtained as in Example 2.

| VOLUME OF CHOLESTEROL SOLUTION APPLIED TO TEST DEVICE | CONCENTRATION OF CHOLESTEROL SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.142 | 0.015 | 0.236 | 0.040 | 0.228 | 0.027 |
| 40 uL | 0.122 | 0.010 | 0.180 | 0.016 | 0.217 | 0.031 |

Figure 12:
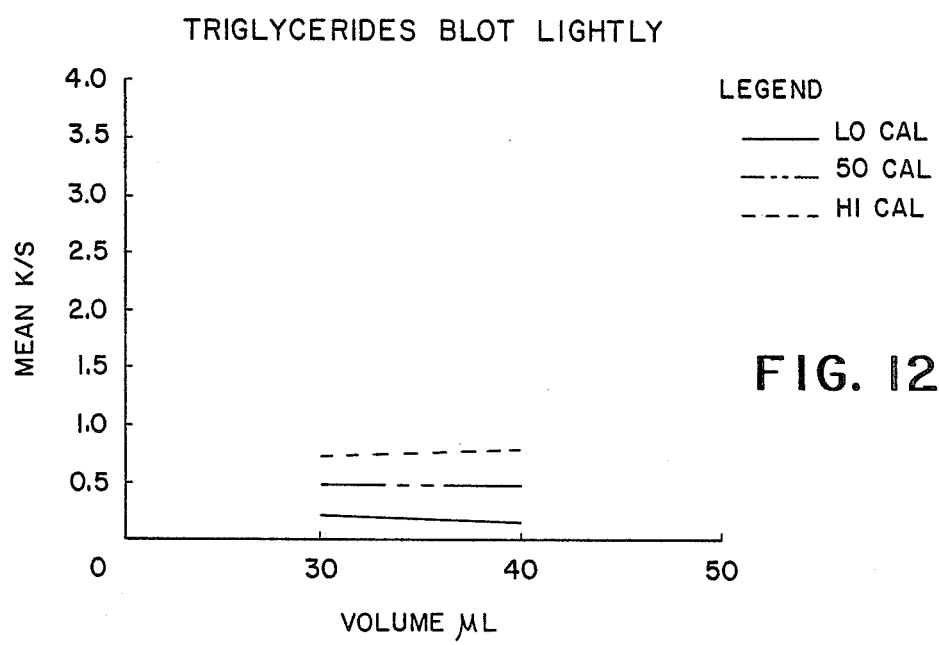

FIG. 12: Data obtained as in Example 3.

| VOLUME OF TRIGLYCERIDE SOLUTION APPLIED TO TEST DEVICE | CONCENTRATION OF TRIGLYCERIDE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.205 | 0.009 | 0.476 | 0.018 | 0.717 | 0.077 |
| 40 uL | 0.156 | 0.017 | 0.478 | 0.044 | 0.791 | 0.032 |

EXAMPLE 15

Potassium Ion Solution Applied to Treated Filter Paper—Blot Lightly Format (3)

Figure 13:
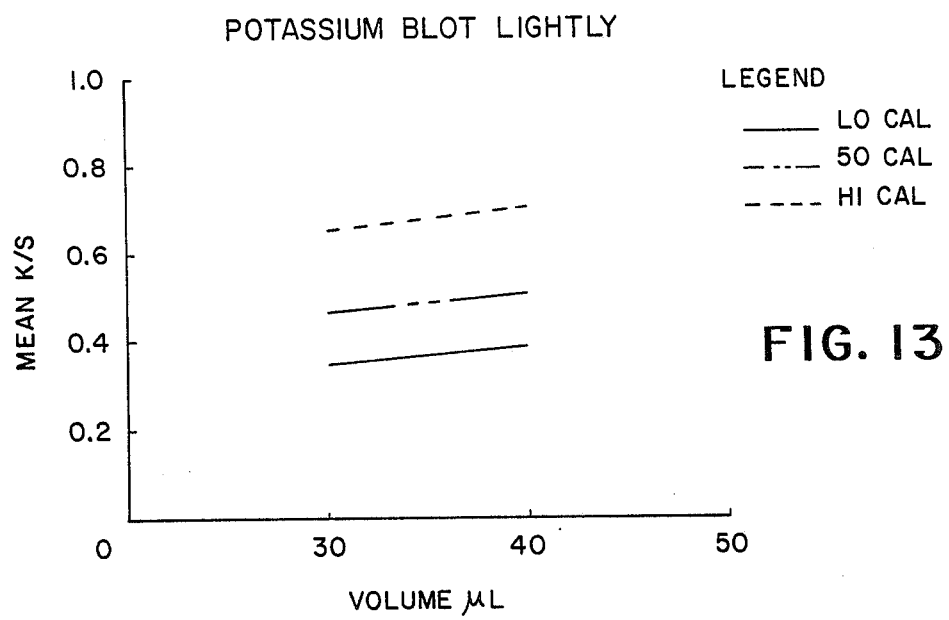

FIG. 13: Data obtained as in Example 4.

EXAMPLE 18

Triglyceride Solution Applied to Treated Filter Paper—Blot Heavily Format (4)

Figure 16:
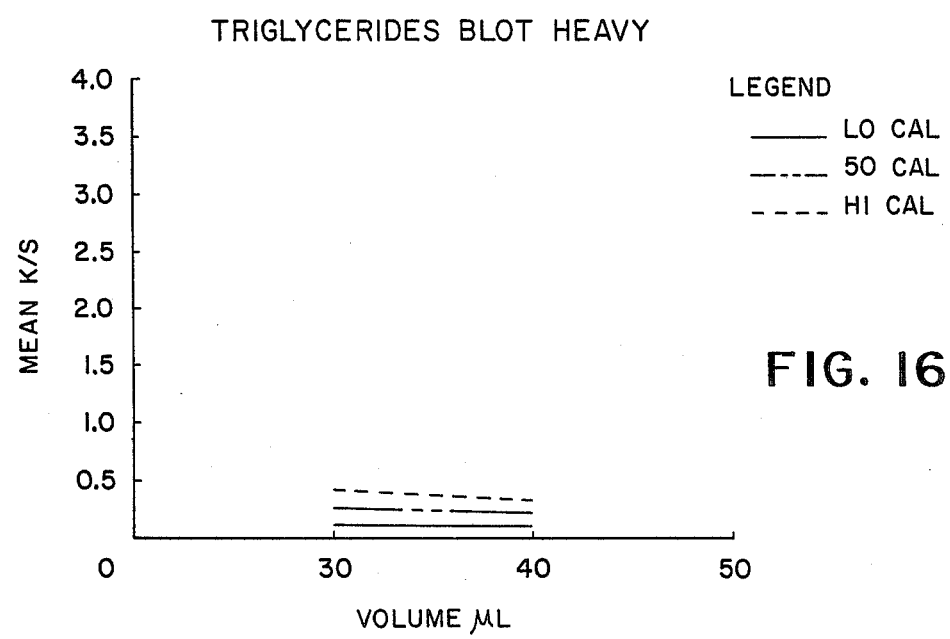

FIG. 16: Data obtained as in Example 3.

| VOLUME OF POTASSIUM ION SOLUTION APPLIED TO TEST DEVICE | CONCENTRATION OF POTASSIUM ION SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.346 | 0.005 | 0.472 | 0.019 | 0.656 | 0.017 |
| 40 uL | 0.395 | 0.004 | 0.512 | 0.004 | 0.711 | 0.013 |

| VOLUME OF TRIGLYCERIDE SOLUTION APPLIED TO TEST DEVICE | CONCENTRATION OF TRIGLYCERIDE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.110 | 0.008 | 0.253 | 0.032 | 0.420 | 0.025 |
| 40 uL | 0.112 | 0.015 | 0.223 | 0.018 | 0.335 | 0.073 |

EXAMPLE 19

Potassium Ion Solution Applied to Treated Filter Paper—Blot Heavily Format (4)

Figure 17:
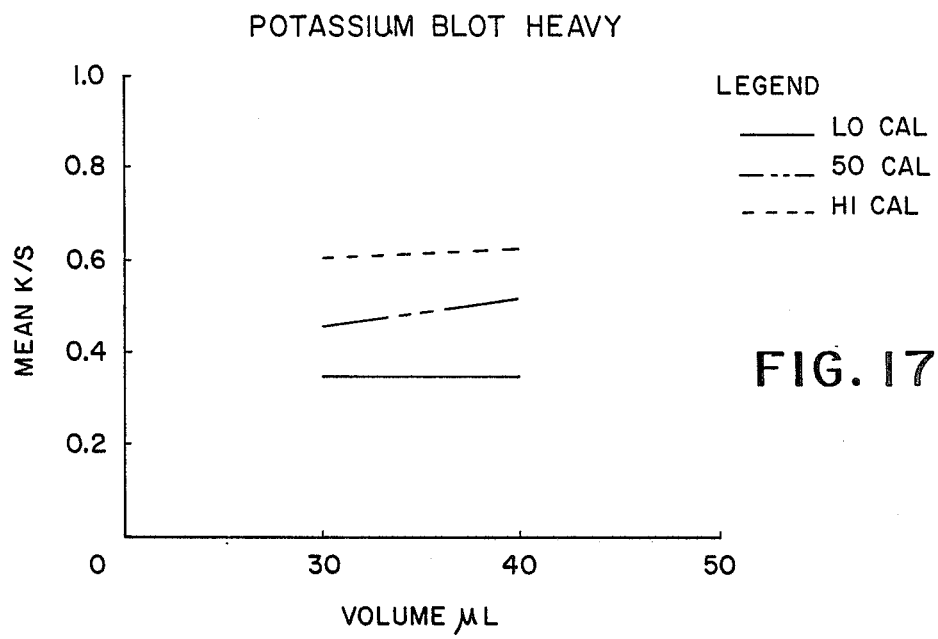

FIG. 17: Data obtained as in Example 4.

| VOLUME OF POTASSIUM ION SOLUTION APPLIED TO TEST DEVICE | CONCENTRATION OF POTASSIUM ION SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.352 | 0.013 | 0.461 | 0.015 | 0.608 | 0.014 |
| 40 uL | 0.351 | 0.010 | 0.515 | 0.002 | 0.629 | 0.010 |

EXAMPLE 20

Glucose Solution Applied to Treated Filter Paper—Blot Heavily Format (4)

Figure 18:
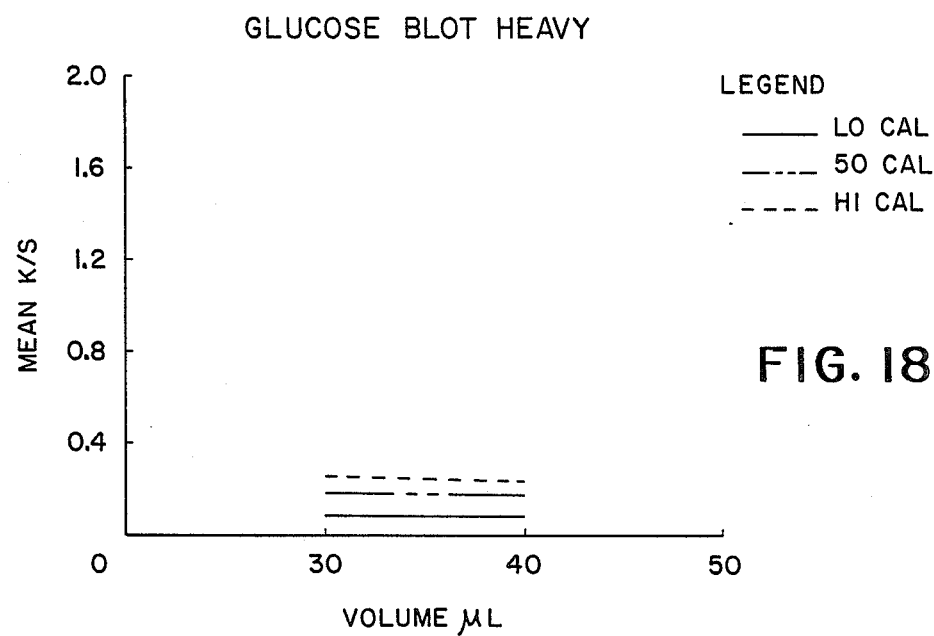

FIG. 18: Data obtained as in Example 5.

| VOLUME OF GLUCOSE SOLUTION APPLIED TO TEST DEVICE | CONCENTRATION OF GLUCOSE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| 30 uL | 0.080 | 0.002 | 0.178 | 0.032 | 0.248 | 0.022 |
| 40 uL | 0.082 | 0.002 | 0.170 | 0.032 | 0.230 | 0.035 |

As shown in Examples 17 through 20 and in FIGS. 15 through 18, the blot heavily technique (4) does reduce the dependence on sample volume compared to the standard control format (0), however, the blotting heavily technique is extremely dependent upon the actual pressure used in blotting. As can be seen by comparing the data and graphs of Examples 17 through 20 to the data and graphs of the blot lightly technique, Examples 13 through 16, the negative slopes of several of the graphed functions in FIGS. 15 through 18 shows the effect of blotting too heavily and thereby removing too much test sample from the bibulous matrix.

EXAMPLE 21

Dye Solution Applied to Untreated Filter Paper—Adjacent Dry Pad Format (5)

Figure 19:
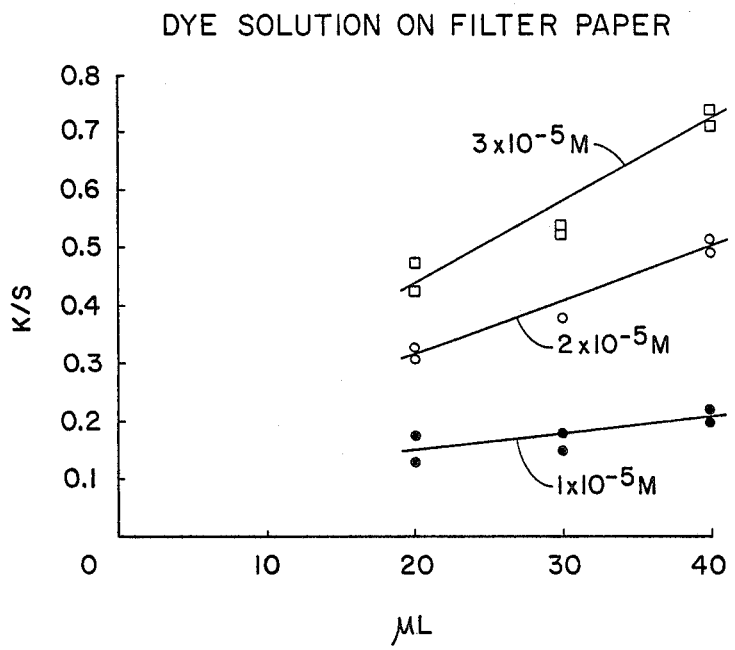

FIG. 19: Data obtained as in Example 1.

| VOLUME OF DYE SOLUTION APPLIED TO TEST DEVICE | CONCENTRATION OF DYE SOLUTION | | | | | |
|---|---|---|---|---|---|---|
| | $1 \times 10^{-5}$ M | | $2 \times 10^{-5}$ M | | $3 \times 10^{-5}$ M | |
| | K/S | STD. DEVIATION | K/S | STD. DEVIATION | K/S | STD. DEVIATION |
| 20 uL | 0.129 | 0.017 | 0.312 | 0.121 | 0.427 | 0.060 |
| | 0.183 | 0.017 | 0.337 | 0.128 | 0.480 | 0.184 |
| 30 uL | 0.187 | 0.016 | 0.368 | 0.008 | 0.535 | 0.026 |
| | 0.161 | 0.011 | 0.363 | 0.010 | 0.525 | 0.004 |
| 40 uL | 0.215 | 0.004 | 0.494 | 0.011 | 0.743 | 0.028 |
| | 0.206 | 0.002 | 0.471 | 0.005 | 0.720 | 0.009 |

As seen from the above data and FIG. 19, the use of an additional bibulous matrix does reduce the dependence upon sample volume. However, the format does not exhibit sample volume independent to a sufficient degree to give accurate and reproducible analytical results on variable test sample volumes. For instance, the K/S values using 40 μL of a $2 \times 10^{-5}$ M dye solution are larger than the K/S values found using 20 μL of $3 \times 10^{-5}$ M solution.

EXAMPLE 22

Dye Solution Applied to Untreated Filter Paper—Adjacent Dry Pad with Bridge Format (6)

Figure 20:
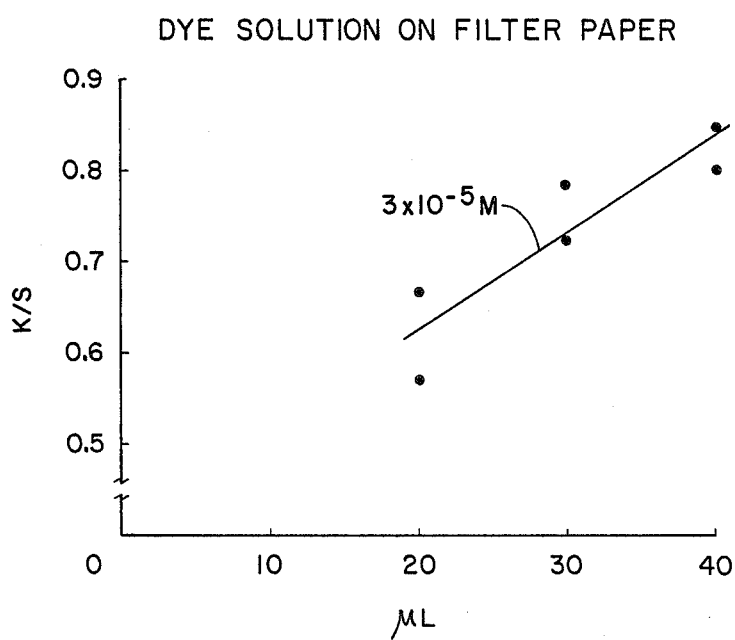

FIG. 20: Data obtained as in Example 1

| VOLUME OF DYE SOLUTION APPLIED TO TEST DEVICE | CONCENTRATION OF DYE SOLUTION $3 \times 10^{-5}$ M | |
|---|---|---|
| | K/S | STD. DEVIATION |
| 20 uL | 0.563 | 0.033 |
| | 0.658 | 0.083 |
| 30 uL | 0.709 | 0.144 |
| | 0.772 | 0.040 |
| 40 uL | 0.797 | 0.014 |
| | 0.848 | 0.033 |

The above data and FIG. 20 shows improved volume independence compared to Example 21 and FIG. 19, however a device based on this format still is not sufficiently volume independent to provide a method and device for giving accurate and reproducible analyte determinations.

EXAMPLE 23

Dye Solution Applied to Untreated Filter Paper—Apply to Adjacent Pad Format (7)

The tests utilizing this format resulted in test sample runover of the test sample from the saturated bibulous substrate to the testing bibulous substrate. Variable amounts of excess test sample were visually present on the testing bibulous substrate. This format essentially did not reduce test sample volume dependence.

EXAMPLE 24

Dye Solution Applied to Untreated Filter Paper—Apply to Adjacent Pad with Bridge Format (8)

The tests utilizing this format resulted in a syphoning of the liquid test sample from the saturated bibulous matrix, across the bridge, to the testing bibulous matrix. Variable amounts of excess test sample were visually present on the testing bibulous matrix. This format essentially did not reduce the test sample volume dependence.

EXAMPLE 25

Cholesterol Solution Applied to Treated Filter Paper—Dip Reagent Format (9)

Data obtained as in Example 2. Volume of applied test solution varies.

EXAMPLE 26

Triglyceride Solution Applied to Treated Filter Paper—Dip Reagent Format (9)

Data obtained as in Example 3. Volume of applied test solution varies.

| | CONCENTRATION OF TRIGLYCERIDE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| Not Quantitatively Measured | 0.310 | 0.009 | 0.746 | 0.021 | 1.212 | 0.031 |

EXAMPLE 27

Potassium Ion Solution Applied to Treated Filter Paper—Dip Reagent Format (9)

Data obtained as in Example 4. Volume of applied test solution varies.

| | CONCENTRATION OF POTASSIUM ION SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| Not Quantitatively Measured | 0.334 | 0.002 | 0.424 | 0.005 | 0.554 | 0.024 |

EXAMPLE 28

Glucose Solution Applied to Treated Filter paper—Dip Reagent Fromat (9)

Data obtained as in Example 5. Volume of applied test solution varies.

| | CONCENTRATION OF GLUCOSE SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| Not Quantitatively Measured | 0.135 | 0.007 | 0.293 | 0.014 | 0.445 | 0.022 |

Examples 25 through 28, using the dip reagent format (9), demonstrate an intrinsically volume indepeddent test method and device because the bibulous matrix in this format can only absorb the volume of liquid test sample to required saturate the matrix. However, for several clinical tests, and in particular for blood serum tests, the dip reagent format (9) is impractical because it requires a large test sample to provide sufficient volume for completely dipping the test device. The dip reagent format also introduces the risk of contamination of the test sample by the diagnostic device, thereby leading to erroneous results or causing interference with any subsequent tests to be run on the same test sample.

| | CONCENTRATION OF CHOLESTEROL SOLUTION | | | | | |
|---|---|---|---|---|---|---|
| | LOW | | MEDIUM | | HIGH | |
| | K/S | STD. DEVIATION | K/S | STD. DEVIATION | K/S | STD. DEVIATION |
| Not Quantitatively Measured | 0.449 | 0.024 | 0.696 | 0.025 | 0.952 | 0.072 |

The summary of results from the data tabulated in Examples 1 through 28 and the graphs in FIGS. 1 through 20 are included in Table II. From the Examples utilizing these various methods and devices, it is seen that several of the devices have formats demonstrating sample volume independence. However, these devices, including the touchoff, blot lightly, blot heavily and dip reagent formats, also have the disadvantages and drawbacks of technique sensitivity, laboriousness or the need of a large sample volume. However, the method of the present invention, using the film cover format, and as illustrated in Examples 6 through 8 and in FIG. 6, shows essentially complete volume independence and is free of any technique or manipulative disadvantages.

In Table II, the volume dependence is expressed relative to the volume dependency of the standard control format (0). For a basis of comparison, the volume dependency of the standard control format was arbitrarily assigned a value of unity. The term "CV" is the coefficient of variation and is determined by multiplying the standard deviation by 100 then dividing by the average K/S value.

TABLE II

| Format Example No. | Nos. | Method | Volume Dependence | Comment |
|---|---|---|---|---|
| 0 | 1–5 | Standard | 1 | Control |
| 1 | 6–8 | Film cover | 0 | Best, CV low |
| 2 | 9–12 | Touch off | 0 | Good, but laborious |
| 3 | 13–16 | Blot lightly | 0 | Technique sensitive |
| 4 | 17–20 | Blot heavily | 0 | Very technique sensitive, high CV |
| 5 | 21 | Adjacent dry pad | 0.5 | Some improvement |
| 6 | 22 | Adjacent dry pad with bridge | 0.25 | More improvement |
| 7 | 23 | Apply to adjacent pad | 1 | No improvement |
| 8 | 24 | Apply to adjacent pad with bridge | 1 | No improvement |
| 9 | 25–28 | Dip reagent | 0 | Requires large sample volume |

As previously described, the device of the present invention includes one or more bibulous matrices covered by a liquid impervious coating or film. The matrices are so treated and arranged to quantitatively determine analyte concentrations in a liquid test sample independent of test sample size. The liquid test sample is deposited on a portion of a bibulous matrix such that the test sample is metered into the bibulous matrix chromatographically. By wicking action, the liquid test sample travels to an assay region of the device that has been previously treated with a suitable test reagent for a particular analyte. In accordance with an important feature of the present invention, the test sample is metered into the bibulous matrices only to the point of liquid saturation of the matrices.

Figure 21:
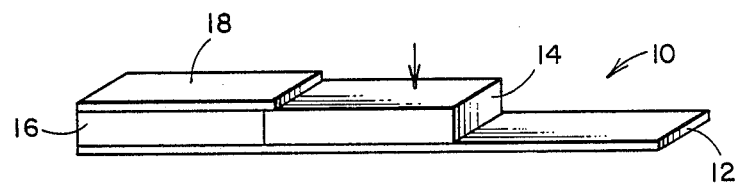
FIG. 21 is a perspective view of a volume independent diagnostic device constructed in accordance with one embodiment of the present invention for determining analyte concentrations in liquid samples having a liquid impervious barrier extending from a portion of the first bibulous matrix and completely covering the second testing matrix and secured to the top of contacting adjacent bibulous matrices to precisely meter test sample from a first matrix to a second testing matrix, and to prevent test sample spillover from the first matrix onto the second testing matrix.

Specifically, the positioning of the bibulous matrices and the testing-reagent, and the metering of the sample, may be better understood by reference to FIGS. 21 through 25. FIG. 21 shows a perspective view of a volume independent diagnostic device 10 including a first bibulous matrix 14; and a second bibulous matrix 16 impregnated with a suitable testing reagent, both bibulous matrices securely adhered to a support strip or handle 12. As will become more apparent hereinafter, in order to facilitate the quantitative determination of analytes, it is preferred that the support strip or handle be manufactured from a hydrophobic material. Preferably, the hydrophobic material is translucent, and can be formed from materials such as cellulose acetate, polyethylene, terephthalate, polycarbonate and polystyrene. A hydrophobic barrier 18 is disposed above the two bibulous matrices 14 and 16 attached to substrate 12 to help meter the test sample into the first bibulous matrix 14 and to prevent sample spillover onto the second bibulous matrix 16. In this embodiment, the hydrophobic barrier 18 is positioned above the bibulous matrices 14 and 16, near the end of the first bibulous matrix 14 that is in contact wth the second bibulous matrix 16. The barrier 18 extends to completely cover the second bibulous substrate 16.

To achieve the full advantage of the present invention, the test sample should be introduced in the area of the arrow. For the arrangement illustrated in FIG. 21, such a placement allows barrier 18 to help meter the sample into the first bibulous matrix 14. The wicking action of bibulous matrix 14 allows the test sample to chromatograph through matrix 14 to the second bibulous matrix 16. Upon saturation of the second bibulous substrate 16 with test sample, no further test sample can be metered into the first bibulous substrate 14. The hydrophobic barrier 18 also prevents spillover of excess test sample onto the second bibulous matrix to prohibit excess sample addition into bibulous matrix 16 and therefore interfere with the chromogenic test within the assay area. If barrier 18 is absent, test sample may run onto and flood bibulous matrix 16 as opposed to chromatographing through the bibulous matrix 14. This results in excess test sample entering the assay area of bibulous matrix 16 yielding inaccurate analyte determinations.

In accordance with an important feature of the present invention, the barrier 18 comprises a liquid impermeable material, such that the test sample cannot penetrate through the barrier 18 to directly contact the second bibulous substrate 16. The barrier 18 is preferably a transparent or translucent material. However, if the substrate 12 is transparent, and readings are taken through substrate 12, then the barrier 18 can be opaque. Suitable materials include tape, silicones, rubber, plastics, and waxes. Waxes that are especially useful are smooth, water repellent and nontoxic. Types of waxes that can be utilized in the method and device of the present invention include natural waxes, such as animal wax, beeswax, spermaceti, lanolin, shellac wax; vegetable waxes, such as carnauba, candelilla, bayberry, sugar cane; mineral waxes, such as fossil or earth waxes, including ozocerite, ceresin, montan; and petroleum waxes, such as paraffin, microcrystalline, petrolatum; as well as synthetic waxes such as ethylenic polymers and polyoletheresters, sorbitol and chlorinated napthalenes and other hydrocarbon waxes.

Figure 22:
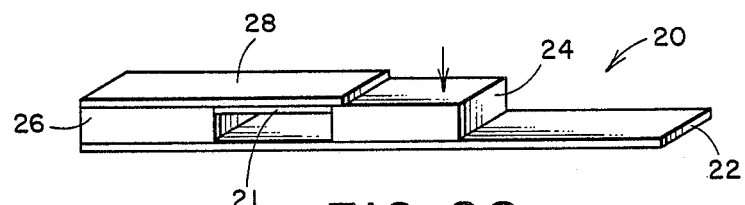
FIG. 22 is a view similar to FIG. 21 showing the first matrix and the second testing matrix separated and connected by a thin, absorbent tissue bridge.

Another configuration of the device 20 of the present invention is illustrated in FIG. 22, wherein the two bibulous matrices 24 and 26 attached to a substrate 22 are not in intimate contact, but physically separated and connected by a bibulous thin-tissue bridge 21, whereby the test sample can travel from the first bibulous matrix 24 to the second bibulous matrix 26 for assay. A hydrophobic barrier 28 is disposed to cover the thin tissue bridge 21 to help meter the sample to the bibulous matrices 24 and 26 and avoid contamination of the assay area by the test sample.

Figure 23:
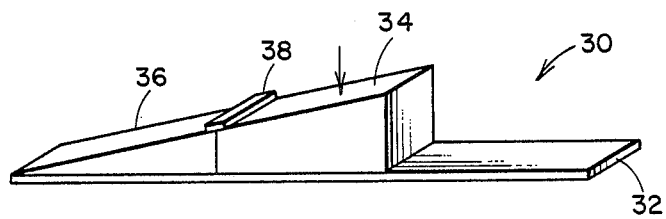
FIGS. 23 and 24 are views similar to FIGS. 21 and 22 showing alternate configurations of the device of the present invention.
Figure 24:
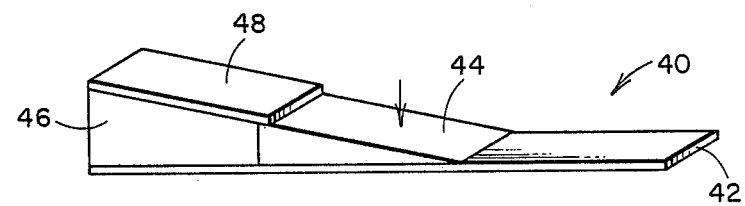

FIGS. 23 and 24 are alternate configurations 30 (40) wherein the amont of the test sample required may be increased or decreased per dose by varying the size of the second bibulous matrix 36 (46) relative to the size of the first bibulous matrix 34 (44). Such configurations attached to substrates 32 (42) and containing a barrier 38 (48) allows flexibility in analyte determinations by making chromogenic reactions more responsive to quantitative determination.

Figure 25:
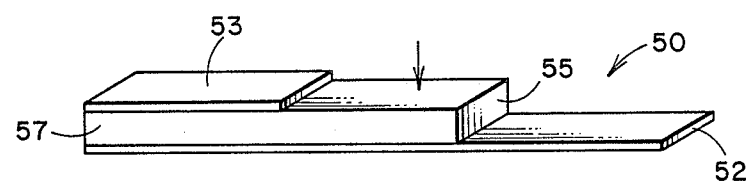
FIG. 25 is a view similar to FIGS. 21-24 showing another construction of the device of the present invention including only one bibulous matrix.

FIG. 25 illustrates a configuration 50 utilizing a single bibulous matrix generally designated 55 attached to a substrate 52. The testing reagent is impregnated in one portion 57 of matrix 55 covered by barrier or coating 53, and the test sample is applied in the area of the arrow. Although a single matrix test device can be constructed as indicated, to achieve the full advantage of the present invention, the device is fabricated such that the test reagent is introduced in an assay area of the bibulous matrix spaced from the area of the bibulous matrix where the test sample is applied.

In accordance with an important feature of the present invention, an excess amount of test sample, usually in excess of approximately 30 microliters, is applied to the diagnostic device in the area of the bibulous matrix that is not covered by the liquid-impervious coating or film. This sample volume is sufficient to provide an excess amount of test sample, thereby assuring saturation of each bibulous matrix. The liquid-impervious barrier helps meter the test sample into the bibulous matrices. The liquid chromatographs through the bibulous matrices by wicking action up to the point of matrix saturation. After matrix saturation by the test sample, the metering and wicking action stops such that no free liquid test sample enters the assay area of the diagnostic device to fill the voids between the materials comprising the bibulous matrix. Therefore, a constant volume of test sample, in relation to the size of the bibulous matrix, is directed to the assay area of the device, resulting in accurate and reproducible analyte concentration determinations.

The pariicular test reagent composition contained in the bibulous matrix depends on the particular analyte to be measured and is within the skill of those in the art. Normally the test reagents are impregnated into the bibulous matrix prior to the attachment of the bibulous matrix to a suitable hydrophobic substrate.

Thus, in accordance with the present invention, the amount of test sample placed onto the diagnostic device is in excess of the sample amount required to saturate the test reagenttreated pad. When the test reagent-treated pad becomes saturated further flow of test sample stops, and the remainder of the test sample remains separated from the reagent pad by the coating or film layer and does not thereby affect the chromogenic reaction.

In accordance with an important feature of the process and device of the present invention, in addition to a constant and reproducible amount of test sample reaching the assay area of the device, the test sample reaches the assay area of the device with an essentially unaltered composition. Tests performed on blood samples showed no increase in potassium ion or loss of cholesterol, as the test sample chromatographed through the bibulous matrices. Generally, the proper amount of test sample has reached the assay area when the assay area is saturated with test sample. This is accomplished by using an excess test sample to assure test sample saturation of the assay area. The size of the test sample can be increased or decreased by adjusting the relative sizes of the first bibulous substrate and the second test reagent-containing bibulous matrix such that the assay area will be saturated with test sample. The sizes of bibulous matrices will depend upon a predetermined test sample size and the testing reagent and method utilized. This process assures an essentially fixed amount of test sample to reach the assay area, and renders more accurate and reproducible analyte determinations. The variables of minimum test sample size, bibulous matrix size, and the amount of test reagent to incorporate into the assay area bibulous matrix easily can be determined by those skilled in the art.

In addition to the fast and efficient analyte determinations of liquid test samples, and the essentially complete migration of unaltered test sample to the assay area, the method and device of the present invention permit quantitative analyte determinations without dilution of the liquid sample. Testing the undiluted serum or plasma both omits a manipulative step and, more importantly, eliminates the possibility of technician error. The proper amount of a suitable chromogenic reagent can be incorporated into the assay area for immediate reaction with the undiluted liquid test sample. The extent of the chromogenic reaction, and therefore the quantitative amount of the analyte, then can be determined by the chromogenic detection techniques that are well-known in the art.

Obviously, many modifications and variations of the invention as hereinbefore set forth can be made without departing from the spirit and scope thereof and therefore only such limitations should be imposed as are indicated by the appended claims.

What is claimed is:

1. A device for metering a constant volume of a liquid to an analyte assay area and for determining analyte concentrations in liquid samples consisting essentially of a first bibulous matrix devoid of reagent; a second bibulous matrix containing a suitable test reagent in a sufficient quantity for interaction with a particular analyte constituent of the liquid to produce a detectable change in the second bibulous matrix upon contact with the liquid, said second bibulous matrix being disposed sufficiently close to the first bibulous matrix and so positioned and sized that the interaction between the analyte constituent of the liquid and the testing reagent is quantitatively detected; and a liquid impermeable barrier disposed over a portion but not all of the first bibulous matrix and at least a portion of the second bibulous matrix such that liquid applied to the first bibulous matrix at an area spaced from the second bibulous matrix will be metered into the second bibulous matrix only to the point of liquid saturation of the second bibulous matrix such that the quantitative determination of the analyte constituent of the liquid is independent of the volume of liquid sample applied to the first bibulous matrix.

2. The device of claim 1 wherein the first bibulous matrix and the second bibulous matrix are the same or different hydrophilic materials selected from the group consisting of inorganic powders, sponge materials, argillaceous materials, cloth, hydrophilic naturally-occurring polymers, hydrophilic naturally-occurring modified polymers, hydrophilic synthetic polymers, silica gel, alumina, diatomaceous earth, cellulosic materials, nitrocellulose, cellulose acetate, polyvinyl chloride, polyacrylamide, polyurethanes, polyacrylates, crosslinked dextran, agarose, and mixtures thereof.

3. The device of claim 2 wherein the first and second bibulous matrices are filter paper.

4. A volume independent diagnostic device comprising at least one bibulous matrix, said bibulous matrix comprising a reagent-treated test area and an area devoid of reagent, the reagent-treated test area of the bibulous matrix being covered by a liquid impermeable barrier, said barrier so positioned to meter a liquid from the test area devoid of reagent to the regent treated test area of the bibulous matrix, wherein bibulous matrix area devoid of reagent permits liquid to pass through the bibulous matrix area devoid of reagent to introduce a constant, saturating amount of liquid into the reagent treated test area.

5. The device of claim 4 wherein the reagent treated test areas of the bibulous matrix and the area of the bibulous matrix devoid of reagent are the same or different hydrophilic materials selected from the group consisting of inorganic powders, sponge materials, argillaceous materials, cloth, hydrophilic naturally-occurring polymers, hydrophilic naturally-occurring modified polymers, hydrophilic synthetic polymers, silica gel, alumina, diatomaceous earth, cellulosic materials, nitrocellulose, cellulose acetate, polyvinyl chloride, polyacrylamide, polyurethanes, polyacrylates, crosslinked dextran, agarose, and mixtures thereof.

6. The device of claim 5 wherein the bibulous matrix is filter paper.

7. A method of determining analyte concentrations in a liquid comprising contacting a first area of a bibulous matrix devoid of reagent with an excess quantity of the liquid, said first area of said bibulous matrix disposed in contact with a second area of bibulous matrix, said second area containing a sufficient quantity of a suitable testing reagent for a particular analyte for interaction with the liquid to produce a detectable change in the second area of the bibulous matrix; said first area of the bibulous matrix and the second area of the bibulous matrix being only partially covered by a liquid-impermeable covering disposed to prevent the liquid from initially contacting an upper surface of the second area of the bibulous matrix, said covering metering the liquid from the first area of the bibulous matrix, under the liquid-impermeable covering to saturate the second area of the bibulous matrix to cause the liquid to interact with the testing reagent resulting in a detectable change in the second area of the bibulous matrix, and detecting the detectable change in said second bibulous matrix in the second area of the bibulous matrix.

8. The method of claim 7 wherein the first bibulous matrix and the second bibulous matrix are the same or different hydrophilic materials selected from the group consisting of inorganic powders, sponge materials, argillaceous materials, cloth, hydrophilic naturally-occurring polymers, hydrophilic naturally-occurring modified polymers, hydrophilic synthetic polymers, silica gel, alumina, diatomaceous earth, cellulosic materials, nitrocellulose, cellulose acetate, polyvinyl chloride, polyacrylamide, polyurethanes, polyacrylates, crosslinked dextran, agarose, and mixtures thereof.

9. The method of claim 8 wherein the first and second bibulous matrices are filter paper.

10. A device for metering a constant volume of a liquid to an analyte assay area comprising a bibulous matrix having upper and lower major surfaces, the lower major surface disposed against a hydrophobic substrate, and the upper major surface being only partially covered by a liquid impermeable barrier, said bibulous matrix having a first portion devoid of reagent and a second portion which is reagent impregnated such that liquid applied to an area of the upper bibulous matrix surface spaced from the liquid-impermeable barrier is metered into the first bubulous matrix portion devoid of reagent, wherein the liquid flows through the first bibulous matrix portion devoid of reagent to saturate the second reagent impregnated bibulous matrix portion in the analyte assay are with a constant volume of liquid per unit volume of the second regaent impregnated bibulous matrix portion.

11. A method of introducing a constant volume of a liquid from a liquid application area to an assay area of a diagnostic device comprising contacting a bibulous matrix devoid of reagent with a quantity of liquid at least sufficient to saturate an assay area of the bibulous matrix containing regent, wherein a liquid-impervious covering is disposed over only a portion of the liquid-application area of the bibulous matrix which is devoid of reagent and over all or a portion of the assay area of the bibulous matrix containing reagent to prevent the liquid from initially contacting the assay area of said bibulous matrix containing reagent and to meter the liquid from the liquid application area to the assay area of said bibulous matrix containing reagent, allowing a quantity of the liquid to flow through said bibulous matrix devoid of reagent and under the liquid-impervious covering, to saturate the assay area of the blibulous matrix containing reagent.

* * * * *